United States Patent [19] [11] 4,166,378
Berger et al. [45] Sep. 4, 1979

[54] METHOD AND APPARATUS FOR THE DIFFERENTIAL THERMAL ANALYSIS OF A MOLTEN METAL

[75] Inventors: Peter Berger, Düsseldorf-Benrath; Milan Lampic, Kaarst; Jörg Müller, Düsseldorf-Wersten; Kurt Orths, Ratingen, all of Fed. Rep. of Germany

[73] Assignee: Verein zur Förderung der Giesserei-Industrie, Düsseldorf, Fed. Rep. of Germany

[21] Appl. No.: 863,328

[22] Filed: Dec. 22, 1977

[51] Int. Cl.² ............................................. G01N 25/04
[52] U.S. Cl. .................................... 73/15 B; 73/17 R
[58] Field of Search ............ 73/15 B, 17 A; 364/472, 364/499, 557, 857

[56] References Cited

U.S. PATENT DOCUMENTS

| 3,891,834 | 6/1975 | Warsinski | 73/17 |
| 4,008,604 | 2/1977 | Roach et al. | 73/17 |
| 4,044,600 | 8/1977 | Claxton et al. | 73/15 |
| 4,046,509 | 9/1977 | Backerud | 73/17 |

Primary Examiner—Herbert Goldstein
Attorney, Agent, or Firm—J. Harold Nissen

[57] ABSTRACT

The invention relates to a method for measuring the cooling curve of a test sample of metal or a metal alloy, in particular cast iron or cast steel, for the differential thermal analysis in which the difference of the cooling curve of the test sample of a fixedly given comparative curve which satisfies Newton's law of cooling ($U = U_0 \cdot \times e^{-t/RC}$, the $U_0$ parameter being the maximum value at the point in time $t = 0$ and the RC parameter being the time constant) is formed, said comparative curve being brought to coincidence with a section of the cooling curve of the sample by adjusting its parameters so that the difference can then be formed between the adjusted comparative curve and the cooling curve.

13 Claims, 3 Drawing Figures

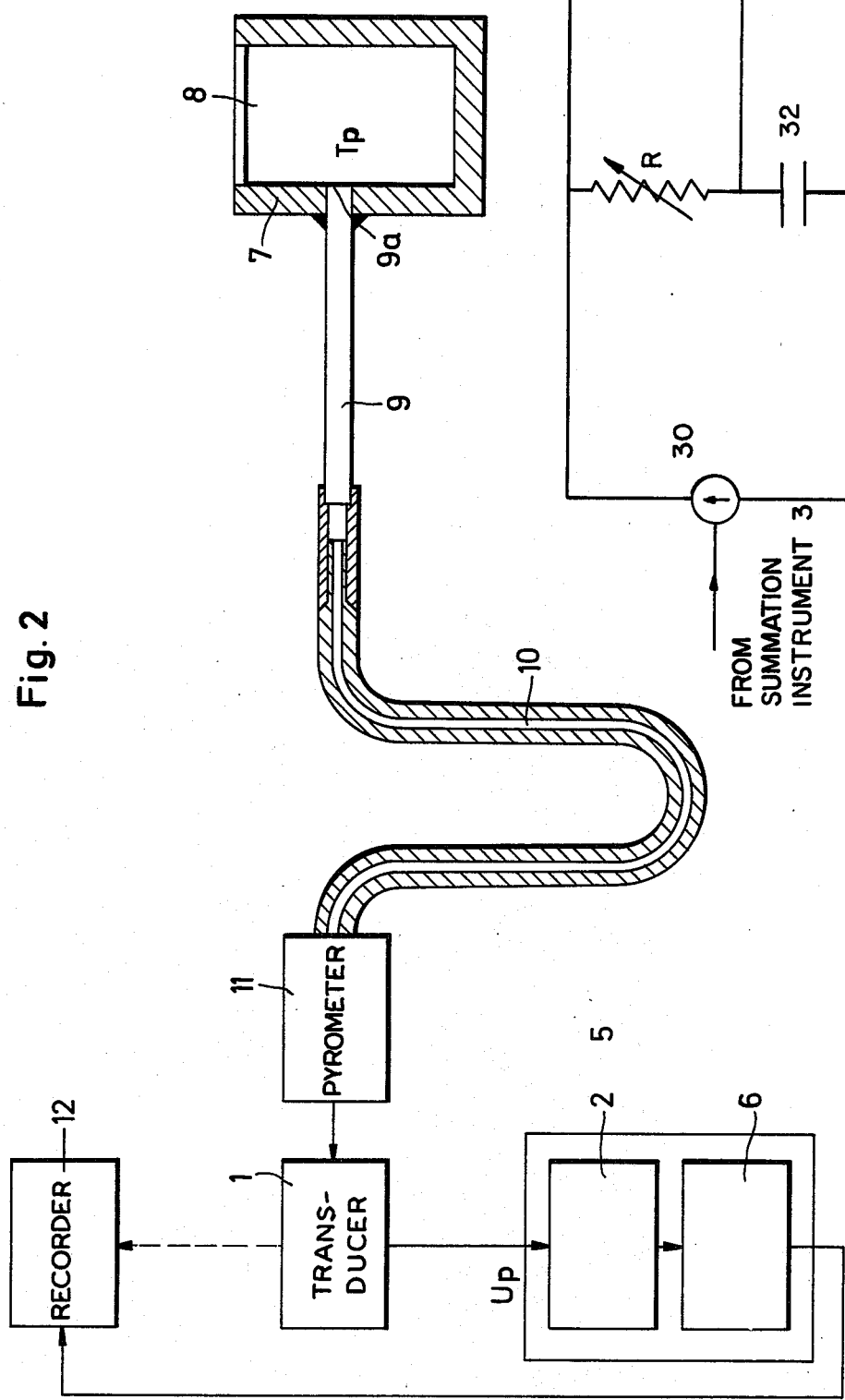

METHOD AND APPARATUS FOR THE DIFFERENTIAL THERMAL ANALYSIS OF A MOLTEN METAL

BACKGROUND AND BRIEF DESCRIPTION OF THE INVENTION

The differential thermal analysis is used in order to be able to draw conclusions on the composition of materials, such as metals and metal alloys among others. It supplies substantially more comprehensive and clearer statements concerning the phase composition of the tested material than the normal thermal analysis (evaluation of time temperature curves). The method itself is carried out in laboratory conditions for test samples with a low microgram mass of up to 10 g. The differential thermal analysis cannot be carried out with conventional DTA (Differential-Thermo-Analysis) devices on test samples with a mass of over 10 g which must generally be used for a quick operational control of metal melts. Neither can the classical differential thermal analysis supply any statements concerning solidification behavior and phase composition of real castings.

In another known, but not used, method of the differential thermal analysis the cooling curve of the test sample is compared with the curve of a group of fixedly given curves which satisfy Newton's law of cooling $U = U_0 \times e^{-t/RC}$, $U_0$ corresponding to the maximum value of the temperature at the point of time $t=0$ and RC being the time constant of the curve. The fixedly given curves are under some circumstances empirically determined taking into consideration all influencing factors (change in material constants and heat transfer conditions during cooling of the test sample to be tested) and stored by computer from which they can be called dependent on the expected cooling curve of the test sample.

In such a method of differential thermal analysis, none of the curves of the group generally coincides fully with the cooling curve of the test sample in the liquid zone. For this reason, this method for metals and metal alloys and, in particular, cast iron and steel, is inaccurate even when interpolation is made between given curves to adapt them to the cooling curve of the test sample.

In another known process an imaginary connecting line between the first and last (at the end) transformations of the test sample, which are characterized by thermal effects, is used as a comparative curve. All the results calculated on the basis of such an approximate curve are affected with systematic faults.

In a known method of the aforementioned type the cooling curve is measured at a fixed test sample with a thermal element. The course of cooling of a fixed test sample, however, does not show any distinct heat effects. It has been attempted to increase the cooling speed in order to compensate this disadvantage. An increased cooling speed, however, is accompanied by difficulties in adjusting the comparative curve. The conclusions in the case of this method are also invalidated by using the thermal element as the measuring detector. That is, thermal elements falsely record the course of cooling of the test sample due to disturbing proximity influences.

The object of the invention is to provide a method of the aforementioned type and an apparatus suited to carrying out the method, both of which are simpler to use and supply more exact differential values than known methods and apparatus.

This object is solved according to the invention in that by using a vessel for molten metal, the cooling curve of the molten test sample is measured on the metal/vessel boundary layer and these measurements are used for adjusting the parameters of the comparative curve.

Very exact difference values are obtained with the method of the invention since the heat effects above all in the molten zone of the curve at the metal/vessel boundary layer are the least inaccurate. The accuracy of the comparison test sample to be adjusted can be further improved by the determined difference values being differentiated.

An apparatus to carry out the method comprises a temperature measuring device and a comparator which records the deviation of the cooling curve of the test sample from a fixedly given comparative curve which is produced by a signal transmitter working according to Newton's law ($U = U_0 \times e^{-t/RC}$, the $U_0$ parameter being the maximum value at the point in time $t=0$ and the RC parameter being the time constant), to which an adjustment means is arranged which, dependent on the parameters determining the cooling curve of the test sample in one curve section, adjusts the corresponding parameters $U_0$ and RC of the comparative curve for the corresponding curve section at the signal transmitter in such a manner that the two curve sections coincide, and is characterized in that the measuring detector of the temperature measuring device includes a light conductor which closes with its front side flush with the inside of the mold hollow space of a casting mold for the molten test sample.

The comparator is preferably constructed in the form of a summation instrument for the deviation of the two curves. In addition, a differentiator can be arranged after the summation instrument.

According to a further embodiment of the invention an elastic bonding agent can be arranged between the light conductor and the casting mold. This bonding agent should on the one hand oppose the ferro-static pressure by sufficient resistance to displacement of the light conductor, but on the other hand not hinder the movement of the light conductor in contraction direction of the metal on solidification and cooling. It has namely been shown that the front side of the light conductor adheres to the surface of the solidified metal block most probably caused by early formation of a narrow metal ridge on the light conductor/casting mold boundary surface which shrinks onto the light conductor and communicates hereto the movements of the metal wall.

According to a further embodiment the light conductor is composed of optical quartz glass for temperatures over 500° C.

The invention is explained below in further detail by means of a drawing representing an embodiment.

BRIEF DESCRIPTION OF THE DRAWINGS

FIG. 2 shows the apparatus according to FIG. 1 together with a measuring detector including a light conductor;

FIG. 3 shows a schematic circuit wiring diagram of a signal generator shown in FIG. 1.

Figure 1:
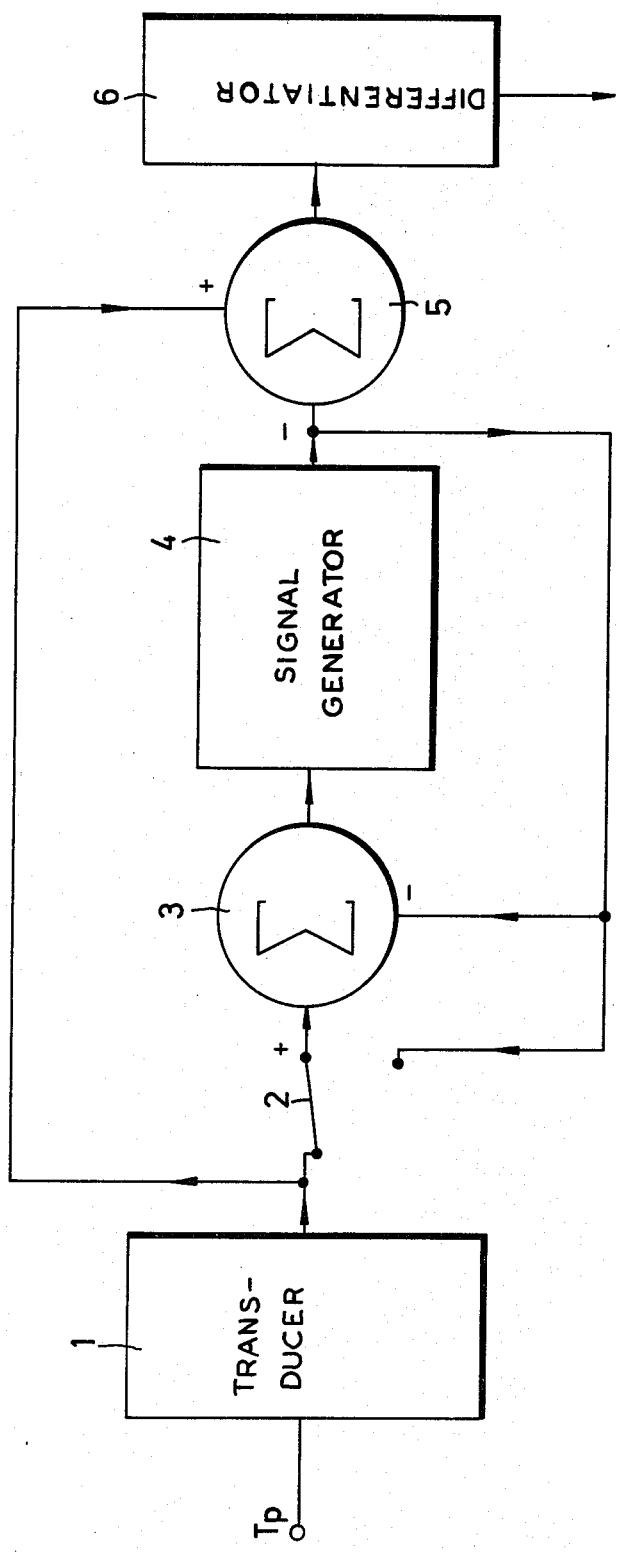
FIG. 1 shows a block diagram of the apparatus for carrying out the thermal analysis.

A transducer 1 transforms the temperature $T_p$ of the test sample established by a heat detector later to be described into a proportional voltage $U_p$. This voltage $U_p$ is transmitted over a closed switch 2 to a summation instrument 3, to which the output signal $U_O \times e^{-t/RC}$ which is delivered by a regulating circuit 4 is supplied to form a difference so that the regulating circuit 4 as input signal receives the difference value between the two aforementioned signals.

The regulating circuit comprises a signal transmitter 10 which delivers the output signal $U = U_O \times e^{-t/RC}$ and an adjustment means which adjusts the parameters $U_O$ and RC of the signal transmitter. In a very simple embodiment the signal transmitter consists of current source 30 having an adjustable output voltage and feeding current to a series combination of an adjustable resistor R and a capacitor 32. The voltage drop of the resistor R represents the desired output signal U. If the output signal U of the regulating circuit 4 deviates from $U_p$ corresponding to the temperature $T_p$ of the test sample at $t=0$, which is established in the summation instrument 3, then the regulating circuit receives an input signal differing from zero which adjusts the voltage of the current source 30 of the signal transmitter by means of the adjustment means in such a way that the output signal becomes $U = U_p = U_O$. Directly after this adjustment the switch 2 is switched over so that the summing member 3 at both inputs receives the output signal of the regulating circuit 4. In the further course of time the output signal then follows the law $U = U_O \times e^{-t/RC}$.

In order now to adjust the second parameter RC (time constant) of the signal transmitter for the purpose of adapting it to the cooling curve of the test sample, the switch 2 is switched back to the point in time $t = t_1$. This time $t_1$ should preferably still lie in the liquid zone of the test sample. When at this time a deviation is determined between the output signal U of the regulating circuit 4 and the signal $U_p$ at the output of the transducer 1 it is noticed in the summation instrument 3 the time constant RC is adapted by means of the adjustment means while maintaining the previously adjusted value $U_O$, so that the output signal of the regulating circuit 4 also coordinates with the signal $U_p$ of the temperature of the test sample at $t_1$. After this adjustment the switch 2 is switched over again so that the summation instrument 3 again receives the output signal of the regulating circuit 4 at both inputs. Due to lacking deviation the regulating circuit 4 supplies an output signal for the further curve which satisfies the law of cooling $U_O \times e^{-t/RC}$. The adjustment of the time constants RC is achieved at resistance R with largest possible capacity of the capacitor 32. A large adjustment area is obtained hereby.

The output signal of the regulating circuit 4 formed in this manner for the comparative curve is compared in a further summation instrument 5 with the signal $U_p$ corresponding to the temperature $T_p$ of the test sample for the purpose of forming the difference. The recorded difference signal over the time is the DTA curve. The difference signal is preferably supplied to a differential member 6 to increase accuracy and said differential member 6 provides the desired DDTA curve (derived differential thermal analysis curve).

With the apparatus of the invention it is of course not only possible to adapt the output signal of the regulating circuit 4 to the cooling curve of the test sample in the liquid zone but also in a zone of lower temperature. Therefore, the invention enables the comparative curve to be derived from each zone of the cooling curve in order to obtain the most exact difference values and differential value possible.

The described apparatus is preferably used together with the light conductor represented in FIG. 2.

The metal 8 situated in a casting mold 7 touches the front side 9a of the reflected optical quartz glass light conductor 9 and communicates its radiation by means of the latter and a further light conductor 10 composed of flexible fibre optics to an infrared radiation pyrometer 11. Further processing of the measured values obtained is then achieved by means of the transducer 1 and the DTA apparatus 2 to 5 and the differential member 6 as described in connection with FIG. 1. The DDTA curve obtained in this manner is registered together with the normal cooling curve by means of a multi-channel recorder 12 (preferably a light beam oscillograph).

The casting mold 7 is sealed with an elastic bonding agent 13 at the outlet of the light conductor 9 which is in principle movably arranged.

The particular advantage of the method of the invention and of the use of the apparatus according to the invention lies in the effect that the advantages of the differential thermal analysis are open for test sample amounts of over 10 g up to the size of the real castings and thereby provides important information which benefits the production and use of castings. What is to be stressed in particular is the use of the apparatus of the invention in connection with optical measurement of the course of cooling of the metal test sample to be tested. It has been shown that cooling curves in zones free from transformation recorded by means of this optical method strictly follow Newton's law of cooling and thereby represent a very exact basis for adapting the comparative curve. The method and apparatus according to the invention on the whole increase the accuracy of measurement.

While a preferred embodiment of the invention has been shown and described herein it will become obvious that numerous omissions, changes and additions may be made in such embodiment without departing from the spirit and scope of present invention.

We claim:

1. Apparatus for thermally analyzing a metal as the metal cools, comprising:
    (a) temperature converting means for converting the decreasing temperature of the metal into corresponding electrical signals that are indicative of the temperature at any one time;
    (b) a signal generator for generating an adjusted variable signal that corresponds to Newton's law of cooling equations for the metal being analyzed, wherein said equations contain preselected parameters,
    said signal generator comprising adjusting means responsive to an error signal for adjusting the parameters in said variable signal so that said variable signal corresponds to the cooling equations for the metal being analyzed;
    (c) and comparing means for comparing said adjusted variable signal with said electrical signals indicative of the temperature of the metal to supply an error signal to said adjusting means representative of the difference between said variable and electrical signals.

2. Apparatus as in claim 1, in which one of said parameters corresponds to the maximum amplitude in said equation.

3. Apparatus as in claim 1, in which one of said parameters corresponds to the time constant in said equation.

4. Apparatus as in claim 1, and a container for the molten metal, said container having an opening, said temperature converting means comprising a light conductor in said container opening, and positioning means for sealing said conductor in said opening with the front end of said conductor flush with the inner wall of said container.

5. Apparatus as in claim 4, in which said positioning means comprises an elastic bonding agent.

6. Apparatus as in claim 4, in which said light conductor comprising optical quartz glass for temperatures above 500° C.

7. Apparatus as in claim 4, in which said temperature converting means further comprises an optical pyrometer connected to said light conductor.

8. Apparatus as in claim 1, in which said comparing means comprises a comparator for producing a signal equal to the difference between variable signal and said electrical signals, and a differentiator for differentiating said difference signal.

9. A method for the differential thermal analysis of a cooling metal comprising producing a signal representative of the comparative curve of the metal that satisfies the equations of Newton's law of cooling by adjusting selected parameters to bring said comparative curve into coincidence with at least a portion of the actual cooling curve of the metal, converting the actual decreasing temperature of the metal into corresponding signals which are proportional to the temperature at any one point in time, producing a difference signal that is representative of the difference between the signals representative of said comparative curve and the actual temperature of the metal at a particular point in time, using said difference signal to adjust said comparative curve signal to coincide with the actual temperature signal of a portion of the cooling period, and comparing the actual temperature signal to said comparative curve signal subsequent to said portion of the cooling period to produce a second difference signal, and adjusting said parameters in response to said second difference signal to cause said comparative curve to coincide with the actual cooling curve of the metal.

10. A method as in claim 9, comprising the step of obtaining said actual cooling curve by measuring the temperature of said metal at the boundary of the metal and the container in which said metal is retained.

11. The method of claim 10, in which said comparative curve is produced by adjusting the maximum amplitude of said comparative curve to the value of said cooling curve at the initiation of said analysis cycle.

12. The method of claim 11, comprising the further step of producing said comparative curve by determining the time constant a predetermined interval after initiation of said analysis cycle.

13. The method of claim 9, comprising the further step of differentiating said difference signal.

* * * * *